(12) United States Patent
Ishimoto et al.

(10) Patent No.: US 9,931,295 B2
(45) Date of Patent: Apr. 3, 2018

(54) STABILIZED PHARMACEUTICAL COMPOSITION

(75) Inventors: Hayato Ishimoto, Kakamigahara (JP);
Tsutomu Harada, Kakamigahara (JP);
Hiroshi Omae, Kakamigahara (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 40 days.

(21) Appl. No.: 12/161,787

(22) PCT Filed: Feb. 22, 2007

(86) PCT No.: PCT/JP2007/053246
§ 371 (c)(1),
(2), (4) Date: Jul. 22, 2008

(87) PCT Pub. No.: WO2007/097386
PCT Pub. Date: Aug. 30, 2007

(65) Prior Publication Data
US 2010/0249426 A1 Sep. 30, 2010

(30) Foreign Application Priority Data
Feb. 22, 2006 (JP) ................. 2006-045569

(51) Int. Cl.
| | |
|---|---|
| *A61K 9/20* | (2006.01) |
| *A61K 31/675* | (2006.01) |
| *A61K 47/02* | (2006.01) |
| *A61K 47/18* | (2017.01) |
| *A61K 9/00* | (2006.01) |
| *A61K 31/4196* | (2006.01) |
| *A61K 31/4439* | (2006.01) |

(52) U.S. Cl.
CPC .......... *A61K 9/0019* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 31/4196* (2013.01); *A61K 31/4439* (2013.01); *A61K 31/675* (2013.01); *A61K 47/02* (2013.01); *A61K 47/18* (2013.01); *A61K 47/183* (2013.01)

(58) Field of Classification Search
None
See application file for complete search history.

(56) References Cited

U.S. PATENT DOCUMENTS

| 5,100,908 | A | 3/1992 | Murata et al. | |
|---|---|---|---|---|
| 6,812,238 | B1 | 11/2004 | Fukuda et al. | |
| 2001/0041691 | A1 | 11/2001 | Ueda et al. | |
| 2002/0062028 | A1 | 5/2002 | Chen et al. | |
| 2004/0007689 | A1* | 1/2004 | Auffret et al. ................. | 252/70 |
| 2006/0116411 | A1 | 6/2006 | Yada et al. | |
| 2006/0264406 | A1* | 11/2006 | Gao et al. ................ | 514/85 |

FOREIGN PATENT DOCUMENTS

| CN | 1474817 A | 2/2004 | | |
|---|---|---|---|---|
| JP | 3-258717 A | 11/1991 | | |
| JP | 10-512599 A | 12/1998 | | |
| JP | 11-228548 A | 8/1999 | | |
| JP | 2000-169372 A | 6/2000 | | |
| JP | 4-198106 A | 7/2002 | | |
| JP | 2003-520235 A | 7/2003 | | |
| JP | 2004-518640 | * | 6/2004 | ............ C07F 9/6639 |
| JP | 2004-518640 A | 6/2004 | | |
| JP | 2005-015474 | * | 1/2005 | ......... A61K 31/4196 |
| JP | 2005-15474 A | 1/2005 | | |
| KR | 10-2004-0020865 A | 3/2004 | | |
| KR | 10-2006-0015745 A | 2/2006 | | |
| WO | WO-97/28169 A1 | 8/1997 | | |
| WO | WO 02/42283 A1 | 5/2002 | | |
| WO | WO 2004/108134 A1 | 12/2004 | | |
| WO | WO-2006/118351 A1 | 11/2006 | | |

OTHER PUBLICATIONS

Machine translation of JP 2004-518640. Submitted with IDS on Jul. 22, 2008.*
Machine translation of JP 2005-015474. Obtained on Sep. 9, 2010 from AIPN website.*
Ueda et al. Bioorg. Med. Chem. Lett. 13 (2003), pp. 3669-3672.*
Jpn. J. Med. Mycol., vol. 45, No. 2, 2004, pp. 77-81.
Ohwada et al., "Design, Synthesis, and Antifungal Activity of a Novel Water Soluble Prodrug of Antifungal Triazole," Bioorganic & Medical Chemistry Letters, vol. 13, 2003, pp. 191-196.
Ichikawa et al., "Optically Active Antifungal Azoles. XII. Synthesis and Antifungal Activity of the Water-Soluble Prodrugs of 1-[(1R,2R)-2-(2,4-Difluorophenyl)-2-hydroxy-1-methyl-3-(1H-1,2,4-triazol-1-yl)propyl]-3-[4-(1H-1-tetrazolyl)phenyl]-2-imidazolidione," Chem. Pharm. Bull., vol. 49, No. 9, 2001, pp. 1102-1109.
Bentley et al., "The Discovery and Process Development of a Commercial Route to the Water Soluble Prodrug, Fosfluconazole", Organic Process Research and Development, vol. 6, No. 2, Jan. 1, 2002, pp. 109-112.

(Continued)

*Primary Examiner* — Alicia L Otton
(74) *Attorney, Agent, or Firm* — Fish & Richardson P.C.

(57) ABSTRACT

It is an object of the present invention to provide a pharmaceutical composition containing a stable azole-based compound, which is useful as an antifungal agent. According to the present invention, the above-mentioned object can be achieved by adding magnesium hydroxide carbonate, triethylamine, arginine, or another such basic substance to an azole-based compound that is unstable in acids. The above-mentioned pharmaceutical composition is stable enough that the compound will not degrade if the temperature, humidity, or other such conditions should change during production or storage. Also, this composition is useful as a therapeutic agent for deep mycoses because systemic administration is possible by applying it to an oral agent or an injection.

11 Claims, No Drawings

(56) References Cited

OTHER PUBLICATIONS

Ueda et al., "Phosphonooxymethyl Prodrugs of the Broad Spectrum Antifungal Azole, Ravuconazole: Synthesis, and Biological Properties", Bioorganic & Medicinal Chemistry Letters, vol. 13, Jan. 1, 2003, pp. 3669-3672.
European Search Report dated Jul. 23, 2009, for corresponding Application No. 07714744.5.
Australian Office Action dated Oct. 31, 2011 in corresponding Australian Application No. 2007218596.
Chinese Office Action, dated Jul. 14, 2011, for Chinese Application No. 201010226427.5.
Response to Chinese Office Action dated Nov. 24, 2011.
Chinese Office Action, dated Jul. 3, 2012, for Chinese Application No. 201010226427.5 with English translation.
Chinese Response, dated Oct. 15, 2012, to Office Action issued in Chinese Application No. 201010226427.5 with English translation.
Canadian Office Action dated Feb. 24, 2012 for corresponding Canadian Application No. 2,640,331.
Canadian Office Action dated Sep. 13, 2012 for Canadian Application No. 2,640,331.
Canadian Response dated Aug. 17, 2012 for Canadian Application No. 2,640,331.
Canadian Response dated Mar. 7, 2013 for Canadian Application No. 2,640,331.
Korean Notice of Allowance dated Feb. 26, 2013 for Korean Application No. 10-2008-7022876 with English translation.
Korean Response dated Oct. 22, 2012 for Korean Application No. 10-2008-7022876 with English translation.
Japanese Response to a Japanese Office Action for JP Application No. 2008-501746 filed Jun. 15, 2012 with English translation.
Decision to Grant a Patent, dated Jul. 18, 2012, for Japanese Application No. 2008-501746, including an English translation thereof.
Chinese Notification of Reexamination, dated Aug. 15, 2013, for Chinese Application No. 201010226427.5 with an English translation.
Office Action for Japanese Application No. 2008-501746, dated Jul. 18, 2012, including an English translation.
Korean Office Action for Korean Application No. 10-2008-7022876 dated Aug. 21, 2012 with English translation.
Response filed Feb. 7, 2012 to Australian Office Action dated Oct. 31, 2011 for corresponding Australian Application No. 2007218596.
Chinese Office Action with the English translation dated Apr. 9, 2012, for Application No. 201010226427.5.
Japanese Office Action with the English translation dated Apr. 19, 2012, for Application No. 2008-501746.
Canadian Notice of Allowance dated Mar. 28, 2013 for CA Patent Application No. 2,640,331, with English translation.
Chinese Response to a Chinese Office Action for CN Application No. 2010-10226427.5 filed Jun. 18, 2012 with English translation.
Chinese Response filed on Nov. 28, 2013 for Chinese Application No. 201010226427.5 with partial English translation.
Indian Office Action (First Examination Report), dated Mar. 20, 2014, for Indian Application No. 6377/DELNP/2008.
Board's Decision for Chinese Application No. 201010226427.5 dated Feb. 26, 2014, with English translation.

\* cited by examiner

STABILIZED PHARMACEUTICAL COMPOSITION

TECHNICAL FIELD

The present invention relates to a pharmaceutical composition containing an azole-based compound and a basic substance. More particularly, the present invention relates to a stable pharmaceutical composition containing a triazole-based compound which is effective in the treatment of fungal infections, and a basic substance.

BACKGROUND ART

Certain types of azole-based compounds are useful as an antifungal agent, and have been used along with antifungal agents based on polyenes, fluoropyrimidine, and candin to treat fungal infections. The azole-based antifungal agents inhibit lanosterol 14α-demethylase and suppress the synthesis of ergosterol, and are therefore believed to bring about impairment of cellular membrane function in fungi. Examples of the known azole-based antifungal agents may include miconazole, ketoconazole, itraconazole, fluconazole, voriconazole, posaconazole, ravuconazole (see Non-Patent Document 1, for example), and the like, and these drugs can be used not only topically, but also by systemic administration (orally or by injection). Therefore, these can be used to treat and prevent invasive aspergillosis, pulmonary candidiasis, fungal meningitis, and other such deep mycoses.

It is known that some of these azole-based antifungal agents are not absorbed in the intestinal tract when taken orally, and therefore do not exhibit their effect. In view of this, there have been attempts at improving absorption by making the compound into an ester (see Patent Documents 1 and 2, for example), or adding a side chain (see Patent Documents 3, 4, and 5, for example).

Patent Document 1: Published Japanese Translation No. 2003-520235 of PCT International Publication Patent Document 2: Published Japanese Translation No. H10-512599 of PCT International Publication Patent Document 3: Japanese Patent Application Laid-open No. H11-228548

Patent Document 4: Japanese Patent Application Laid-open No. 2000-169372

Patent Document 5: U.S. Pat. No. 6,812,238

Non-Patent Document 1: Jpn. J. Med. Mycol., 45 (2), 2004

DISCLOSURE OF INVENTION

Problems to be Solved by the Invention

However, modifying the compound as above is not necessarily favorable from the standpoint of stability when the azole-based antifungal agents that have undergone such modification is formulated and stored. Therefore, it is an object of the present invention to provide a pharmaceutical composition that remains stable when the azole-based antifungal agents that have undergone such modification are formulated.

Means for Solving the Problems

In view of this, and in light of the above situation, the inventors conducted diligent study aimed at stabilizing the formulation of the azole-based antifungal agents, whereupon they perfected the present invention upon realizing that the specific azole-based antifungal agent are unstable in acids.

Specifically, in a first aspect of the present invention there are provided:

[1] a pharmaceutical composition, comprising:
an azole-based compound that is unstable in an acid, or a pharmacologically acceptable salt thereof; and
a basic substance,

[2] the pharmaceutical composition according to item [1], wherein the azole-based compound is a triazole-based compound,

[3] the pharmaceutical composition according to item [2], wherein the triazole-based compound is at least one selected from the group consisting of
(2R,3S)-2-(2,4-difluorophenyl)-3-(5-fluoro-4-pyrimidinyl)-1-(1H-1,2,4-triazol-1-yl)-2-butyl dihydrogenphosphate,
2-(2,4-difluorophenyl)-1,3-bis(1H-1,2,4-triazol-1-yl)-2-propyl dihydrogenphosphate,
4-[(acetyloxy)methyl]-1-[(2R,3R)-2-(2,4-difluorophenyl)-2-hydroxy-3-[2-oxo-3-[4-(1H-tetrazolyl-1-yl)phenyl]-1-imidazolidinyl]butyl]-1H-1,2,4-triazolium chloride,
4-[[[N-methyl-N-3-[(methylamino)acetoxymethyl]pyridin-2-yl]carbamoyloxy]ethan-1-yl]-1-[(2R,3R)-2-(2,5-difluorophenyl)-2-hydroxy-3-[4-(4-cyanophenyl)thiazol-2-yl]butyl]-1H-1,2,4-triazol-4-ium chloride hydrochloride,
[2-[4-(4-cyanophenyl)-1,3-thiazol-2-yl]-1-(2,4-difluorophenyl)-1-(1H-1,2,4-triazol-1-ylmethyl)propyl]oxy]methyl dihydrogenphosphate, and
pharmacologically acceptable salts of the foregoing,

[4] the pharmaceutical composition according to item [3], wherein the pharmacologically acceptable salt of 2-[4-(4-cyanophenyl)-1,3-thiazol-2-yl]-1-(2,4-difluorophenyl)-1-(1H-1,2,4-triazol-1-ylmethyl)propyl]oxy]methyl dihydrogenphosphate is
a [2-[4-(4-cyanophenyl)-1,3-thiazol-2-yl]-1-(2,4-difluorophenyl)-1-(1H-1,2,4-triazol-1-ylmethyl)propyl]oxy] methyl dihydrogenphosphate monolysine salt or
a [2-[4-(4-cyanophenyl)-1,3-thiazol-2-yl]-1-(2,4-difluorophenyl)-1-(1H-1,2,4-triazol-1-ylmethyl)propyl]oxy] methyl dihydrogenphosphate dilysine salt,

[5] the pharmaceutical composition according to any one of items [1] to [4], wherein the basic substance is an inorganic base, an organic base, a basic amino acid, or a basic macromolecule,

[6] the pharmaceutical composition according to item [5], wherein the basic substance exhibits a pH of at least 8.0 when made into a 1% aqueous solution or a 1% aqueous suspension,

[7] the pharmaceutical composition according to item [5], wherein the basic substance exhibits a pH of at least 10.0 when made into a 1% aqueous solution or a 1% aqueous suspension,

[8] the pharmaceutical composition according to any one of items [5] to [7], wherein the inorganic base is a metal oxide or a metal hydroxide, or a mixture of these, or a complex of the foregoing,

[9] the pharmaceutical composition according to any one of items [5] to [8], wherein the inorganic base is at least one selected from the group consisting of magnesium hydroxide carbonate, sodium hydrogencarbonate, potassium hydrogencarbonate, potassium carbonate, sodium carbonate, magnesium carbonate, calcium carbonate, barium carbonate, magnesium hydroxide, sodium hydroxide, potassium hydroxide, lithium hydroxide, calcium hydroxide, dried aluminum hydroxide gel, magnesium oxide, calcium oxide, barium oxide, calcium silicate, magnesium silicate, magnesium aluminum silicate, magnesium metasilicate-aluminate, sodium hydrogenphosphate, sodium dihydrogenphosphate, synthetic hydrotalcite, a co-precipitate of aluminum hydroxide and magnesium hydroxide, a co-precipitate of aluminum hydroxide, magnesium carbonate and calcium carbonate, and a co-precipitate of aluminum hydroxide and sodium hydrogencarbonate,

[10] the pharmaceutical composition according to any one of items [5] to [8], wherein the inorganic base is at least one selected from the group consisting of magnesium hydroxide carbonate, magnesium oxide, sodium hydroxide, potassium, hydroxide, calcium hydroxide, magnesium hydroxide, sodium carbonate, potassium carbonate, calcium carbonate, magnesium carbonate, sodium hydrogencarbonate, potassium hydrogencarbonate, calcium oxide, and calcium silicate,

[11] the pharmaceutical composition according to any one of items [5] to [8], wherein the inorganic base is at least one selected from the group consisting of magnesium hydroxide carbonate, magnesium oxide, magnesium hydroxide, sodium carbonate, calcium carbonate, sodium hydrogencarbonate, and calcium silicate,

[12] the pharmaceutical composition according to item [5], wherein the organic base is at least one selected from the group consisting of calcium stearate, magnesium stearate, sodium stearate, stearyl sodium fumarate, trisodium citrate, sodium benzoate, monoethanolamine, diethanolamine, triethanolamine, tributylamine, dicyclohexylmethylamine, N-methylpyrrolidine, and meglumine,

[13] the pharmaceutical composition according to item [5], wherein the basic amino acid is at least one selected from the group consisting of lysine, ornithine, histidine, and arginine,

[14] the pharmaceutical composition according to item [5], wherein the basic macromolecule is at least one selected from the group consisting of aminoalkyl methacrylate copolymer E, polyvinyl acetal diethylaminoacetate, and ethyl cellulose,

[15] the pharmaceutical composition according to any one of items [1] to [14], wherein the pharmaceutical composition is an antifungal agent.

In a second aspect of the present invention, there is provided:

[16] a method for stabilizing a pharmaceutical composition, the method comprising the step of mixing a basic substance with an azole-based compound or a pharmacologically acceptable salt thereof.

In a third aspect of the present invention, there is provided:

[17] a process for producing a pharmaceutical composition, the process comprising the step of: mixing a basic substance with an azole-based compound or a pharmacologically acceptable salt thereof.

According to the present invention, a stable pharmaceutical composition containing the azole-based compound having an antifungal action can be obtained. The pharmaceutical composition according to the present invention is absorbed well into the body, and exhibits an excellent antifungal action. According to the present invention, stable tablets, granules, capsules, and the like can also be produced, so that the antifungal agent can be given by systemic administration by an easy method.

BEST MODE FOR CARRYING OUT THE INVENTION

The meaning of the terms, etc., used in this specification and the present invention will be described in detail with reference to embodiments, etc., of the invention.

The pharmaceutical composition according to the present invention contains an azole-based compound that is unstable in acids, or a pharmacologically acceptable salt thereof, and a basic substance. The term "an azole-based compound that is unstable in acids" as used herein means that residual ratio of the compound will fall when the compound is blended and stored in the formulation under the absence of the basic substance, whereas adding a basic substance will inhibit falling residual ratio of the compound.

Of these compounds, specific favorable examples of the azole-based compounds that are unstable in acids and that are used in the present invention may include triazole-based compounds having an antifungal action and pharmacologically acceptable salts thereof. More favorable examples may include the compounds disclosed in Published Japanese Translation No. 2003-520235 of PCT International Publication, and (2R,3S)-2-(2,4-difluorophenyl)-3-(5-fluoro-4-pyrimidinyl)-1-(1H-1,2,4-triazol-1-yl)-2-butyl dihydrogenphosphate (voriconazole dihydrogenphosphate), 2-(2,4-difluorophenyl)-1,3-bis(1H-1,2,4-triazol-1-yl)-2-propyl dihydrogenphosphate (fosfluconazole), 4-[(acetyloxy)methyl]-1-[(2R,3R)-2-(2,4-difluorophenyl)-2-hydroxy-3-[2-oxo-3-[4-(1H-tetrazolyl-1-yl)phenyl]-1-imidazolidinyl]butyl]-1H-1,2,4-triazolium chloride (TAK-457), 4-[[[N-methyl-N-3-[(methylamino)acetoxymethyl]pyridin-2-yl]carbamoyloxy]ethan-1-yl]-1-[(2R,3R)-2-(2,5-difluorophenyl)-2-hydroxy-3-[4-(4-cyanophenyl)thiazol-2-yl]butyl]-1H-1,2,4-triazol-4-ium chloride hydrochloride (BAL8557), and the [2-[4-(4-cyanophenyl)-1,3-thiazol-2-yl]-1-(2,4-difluorophenyl)-1-(1H-1,2,4-triazol-1-ylmethyl)propyl]oxy]methyl dihydrogenphosphate represented by the following Formula (1). These compounds may be in racemic form, or may be R forms, S forms, or other optically active forms.

Of these, [(1R,2R)-2-[4-(4-cyanophenyl)-1,3-thiazol-2-yl]-1-(2,4-difluorophenyl)-1-(1H-1,2,4-triazol-1-ylmethyl)propyl]oxy]methyl dihydrogen phosphate or a monolysine salt or dilysine salt thereof is preferred. The compound represented by Formula (1) can be synthesized by the method discussed in Published Japanese Translation No. 2003-520235 of PCT International Publication.

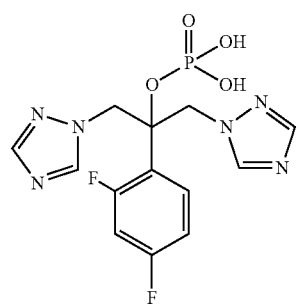

Fosfluconazole

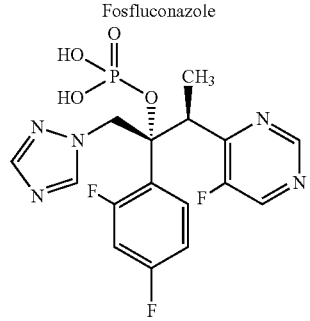

Voriconazole hydrogen phosphate

-continued

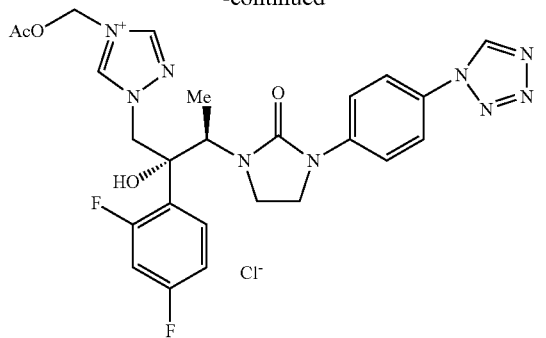

TAK-457

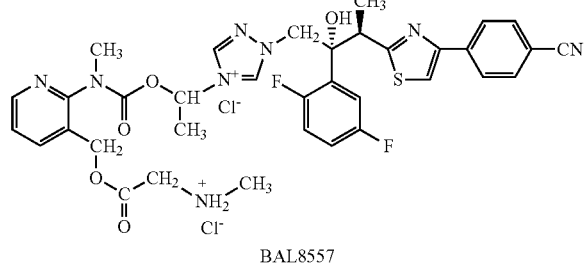

BAL8557

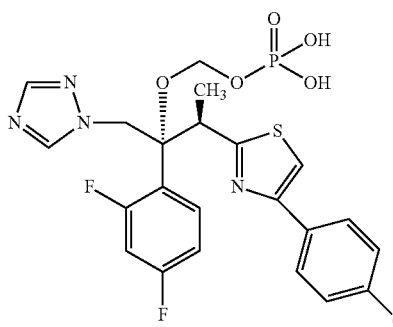

(1)

There are no particular restrictions on the salts of the above compounds as long as they are pharmacologically acceptable, but examples of the salts may include salts of inorganic bases, salts of organic bases, and salts of basic amino acids.

Specific examples of salts of inorganic bases may include alkali metal salts such as sodium salts, potassium salts and the like; alkaline earth metal salts such as calcium salts, magnesium salts and the like; ammonium salts or the like.

Specific examples of salts of organic bases may include salts of alkylamines such as trimethylamine, triethylamine or the like; salts of alkanolamines such as ethanolamine, diethanolamine, triethanolamine or the like; salts of heterocyclic amines such as pyridine, picoline or the like; dicyclohexylamine, N,N'-dibenzylethylenediamine, and the like.

Specific examples of salts of basic amino acids may include salts of lysine, ornithine, histidine, and arginine. Of these salts, mono-, di-, and tri-salts of amino acids are preferable, and monolysine salts are particularly favorable.

Specific examples of basic substances that can be used in the present invention may include inorganic bases, organic bases, basic amino acids, and basic macromolecules. Two or more of these basic substances may also be used in combination. The basic substance used in the present invention preferably exhibits a pH of at least 7, more preferably exhibits a pH of at least 8, and even more preferably a pH of at least 10, when made into a 1% aqueous solution or suspension.

Specific examples of inorganic bases may include magnesium hydroxide carbonate, potassium hydrogencarbonate, sodium hydrogencarbonate, potassium carbonate, sodium carbonate, magnesium carbonate, calcium carbonate, barium carbonate, magnesium bicarbonate, precipitated calcium carbonate, lithium hydroxide, potassium hydroxide, sodium hydroxide, magnesium hydroxide, calcium hydroxide, magnesium-alumina hydroxide, dried aluminum hydroxide gel, magnesium oxide, calcium oxide, barium oxide, calcium silicate, magnesium silicate, magnesium aluminum silicate, magnesium aluminate, magnesium metasilicate-aluminate, sodium hydrogenphosphate, sodium dihydrogenphosphate, synthetic hydrotalcite, a co-precipitate of aluminum hydroxide and magnesium hydroxide, a co-precipitate of aluminum hydroxide, magnesium carbonate and calcium carbonate, and a co-precipitate of aluminum hydroxide and sodium hydrogencarbonate or the like. Magnesium hydroxide carbonate, magnesium oxide, magnesium hydroxide, sodium carbonate, calcium carbonate, sodium hydrogencarbonate, and calcium silicate are preferable, and magnesium hydroxide carbonate, magnesium hydroxide, magnesium oxide, and sodium hydrogencarbonate are especially favorable.

Specific examples of organic bases may include calcium stearate, magnesium stearate, sodium stearate, stearyl sodium fumarate, trisodium citrate, sodium benzoate, monoethanolamine, diethanolamine, triethanolamine, tributylamine, dicyclohexylmethylamine, N-methylpyrrolidine or the like. Calcium stearate, trisodium citrate, and sodium benzoate are preferable, and sodium benzoate is especially favorable.

Specific examples of basic amino acids may include lysine, ornithine, histidine, arginine or the like. Lysine and arginine are preferable, and arginine is especially favorable.

Specific examples of basic macromolecules may include aminoalkyl methacrylate copolymer E, polyvinyl acetal diethylaminoacetate, ethyl cellulose or the like.

In the pharmaceutical composition according to the present invention, an amount in which the basic substance is contained is from 0.001 to 1 parts by weight, preferably from 0.01 to 0.5 parts by weight, and even more preferably from 0.02 to 0.25 parts by weight, based on one part by weight of the azole-based compound.

The pharmaceutical composition according to the present invention can be used in the form of oral agents such as a tablet, a capsule, granules, fine granules, a powder, a liquid, a syrup, a chewable, a lozenge, or the like; topical agents such as an ointment, a gel, a cream, a plaster or the like; an injection; a sublingual tablet; an inhalant; an eye drop; a suppository; or any other form. Tablets, capsules, powders, granules, and injections are preferred.

The pharmaceutical composition according to the present invention can be produced by the known method, such as the method discussed in General Guidelines for Preparations given in Japanese Pharmacopoeia, 14th Edition. For example, in the case of granules, an excipient, binder, disintegrant, solvent, etc., are added as needed to the azole-based compound and subjected to stir granulation, extrusion granulation, tumble granulation, fluidized bed granulation, spray granulation, or the like. Alternatively, water or a binder solution of sucrose, hydroxypropyl cellulose, hydroxypropyl methyl cellulose, or the like may be sprayed onto the core substance such as spherical granules of refined sugar, spherical granules of lactose/crystalline cellulose, spherical granules of sucrose/starch, granular crystalline cellulose or the like, while coating with a powder containing the azole-based compound and additives such as cornstarch, crystalline cellulose, hydroxypropyl cellulose, methyl cellulose, polyvinylpyrrolidone or the like. The granules may also be sized and pulverized.

An excipient, binder, disintegrant, lubricant, antioxidant, flavoring, coloring, essence, or the like may be added as needed to the granules produced as above, and this product made into tablets. Also, a necessary excipient may be added to the raw material azole-based compound or pharmacologically acceptable salt thereof and this product directly made into tablets. Also, capsules can be filled with the above-mentioned granules or with the product of adding and mixing the excipient such as lactose, sucrose, glucose, starch, microcrystalline cellulose, powdered licorice, mannitol, calcium phosphate, calcium sulfate or the like.

Specific examples of excipients may include lactose, sucrose, glucose, fructose, starch, potato starch, cornstarch, wheat starch, rice starch, crystalline cellulose, microcrystalline cellulose, powdered licorice, mannitol, erythritol, maltitol, sorbitol, trehalose, silicic anhydride, calcium silicate, sodium hydrogenphosphate, calcium phosphate, anhydrous calcium phosphate, calcium sulfate or the like.

Specific examples of binders may include gelatin, starch, gum arabic, tragacanth gum, carboxymethyl cellulose, hydroxypropyl cellulose, hydroxypropyl methyl cellulose, polyvinylpyrrolidone, methyl cellulose, partially α-converted starch, α-converted starch, polyvinyl alcohol, sodium alginate, pullulan, glycerol or the like.

Specific examples of disintegrants may include amino acids, starch, cornstarch, calcium carbonate, carmellose, carmellose calcium, croscarmellose sodium, low-substituted hydroxypropyl cellulose, hydroxypropyl starch, crospovidone or the like.

Specific examples of lubricants may include magnesium stearate, stearic acid, calcium stearate, stearyl sodium fumarate, talc, Macrogol or the like.

Specific examples of antioxidants may include sodium ascorbate, L-cysteine, sodium sulfite, tocopherol, soy lecithin or the like.

Specific examples of flavorings may include citric acid, ascorbic acid, tartaric acid, malic acid, aspartame, acesulfame potassium, thaumatin, saccharine sodium, glycyrrhizin dipotassium, sodium glutamate, sodium 5'-inosinate, sodium 5'-guanylate or the like.

Specific examples of colorings may include titanium oxide, ferric sesquioxide, yellow ferric sesquioxide, cochineal, carmine, riboflavin, Food Yellow No. 5, Food Blue No. 2 or the like.

Specific examples of essences may include lemon oil, orange oil, menthol, Japanese mint oil, borneol, vanilla extract or the like.

Similarly, the known method may be employed in producing a liquid. The active ingredient, the azole-based compound or pharmacologically acceptable salt thereof, is dissolved in a solvent such as purified water, ethanol or the like, and a surfactant, anti-foaming agent, or the like may be added as needed.

Specific examples of surfactants may include Polysorbate 80, a copolymer of polyoxyethylene and polyoxypropylene, sodium laurylsulfate or the like.

Specific examples of anti-foaming agents may include glycerol fatty acid esters, sucrose fatty acid esters, sorbitan fatty acid esters, sorbitan trioleate or the like.

The pharmaceutical composition according to the present invention has excellent antifungal action against fungi of the genera *candida, aspergillus, cryptococcus, tricophyton, epidermophyton, microsporum, histoplasma, blastomyces, coccidioides* or the like.

The pharmaceutical composition according to the present invention is useful in the treatment and prevention of fungal infections in animals, and particularly mammals, and more specifically humans. Therefore, the pharmaceutical composition according to the present invention can be administered to mammals, and particularly humans, and while the dosage of the azole-based compound or pharmacologically acceptable salt thereof that is the compositional component thereof will vary with the activity of the individual preparations, the conditions, ages, weights, etc., of the patient, and various other conditions, in the case of oral administration of tablets, capsules, granules, a powder, a syrup, or the like, the dosage is from 10 to 2000 mg/day, and preferably from 100 to 1000 mg/day; in the case of a suppository, it is from 10 to 2000 mg/day, and preferably from 100 to 1000 mg/day; and in the case of an injection, it is from 1 to 1000 mg/day, and preferably from 10 to 500 mg/day.

EXAMPLES

The present invention will now be described in further detail by giving examples and comparative examples, but these are merely illustrative in purpose, and the present invention is not limited to the following specific examples. A person skilled in the art will be able to carry out the present invention by making various changes to the examples given below, and such changes are encompassed by the claims of this patent application.

Production Example 1

Di-tert-butyl-{[(1R,2R)-2-(4-cyanophenyl)-1,3-thiazol-2-yl]-1-(2,4-difluorophenyl)-1-(1H-1,2,4-triazol-1-ylmethyl)propyl}oxy]methyl phosphate

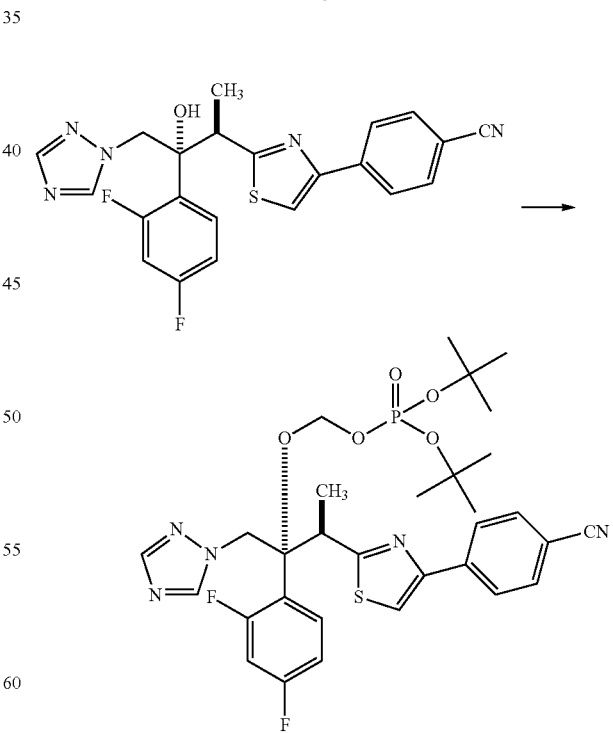

17.77 g (0.46 mol) of 62% sodium hydride was weighed out in a 2 L four-neck flask, and 113 mL of tetrahydrofuran was added under a nitrogen atmosphere. The bath temperature was set to −5° C., and then stirred for 12 minutes, after which 113 mL of a tetrahydrofuran solution in which 20.44 g (0.080 mol) of iodine had been dissolved was added dropwise thereto. The bath temperature was set to 20° C., and then stirred for 78 minutes, after which the bath temperature was brought back down to −5° C., and then stirred for 65 minutes. 289 mL of a tetrahydrofuran solution in which 70.5 g (0.16 mol) of 4-{2-[(1R,2R)-2-(2,4-difluorophenyl)-2-hydroxy-1-methyl-3-(1H-1,2,4-triazol-1-yl)propyl]-1,3-thiazol-4-yl}benzonitrile had been dissolved was added dropwise over a period of 16 minutes, after which the reaction mixture was stirred for 48 minutes at a bath temperature of −5° C. 7 mL of a tetrahydrofuran solution containing 64.36 g of di-tert-butyl chloromethyl phosphate was added, the bath temperature was set to 20° C., and then stirred overnight. The bath temperature was then set to −5° C. to cool the system, after which 529 mL of tert-butyl methyl ether containing 3.2 g of phosphoric acid was added dropwise over a period of 24 minutes. After 90 minutes of stirring, 352 mL of water was added, then another 352 mL of water was added, and liquid separation occurred. This product was then washed with 704 mL of a 2% NaOH aqueous solution, saline, and then water, after which 3.20 g of N-methylmorpholine was added to the separated organic layer, and this product was concentrated under a reduced pressure at a bath temperature of 30° C., which gave 196 g (net weight 100 g content) of the titled compound.

Production Example 2

[(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl dihydrogenphosphate monolysine salt

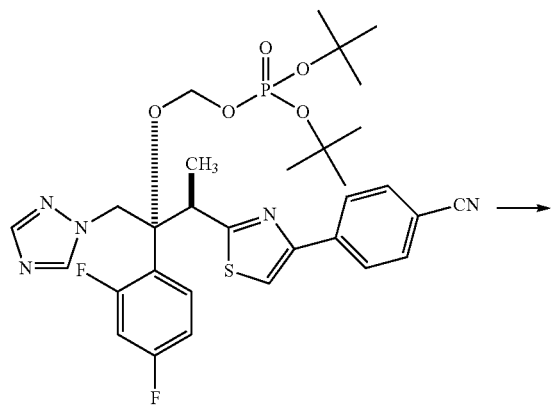

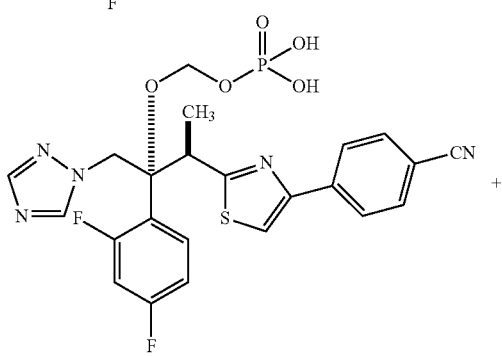

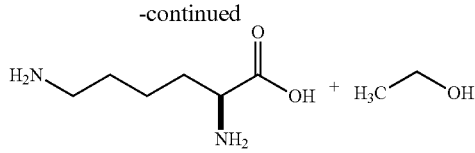

196 g (0.15 mol) of the crude di-tert-butyl-{[(1R,2R)-2-(4-cyanophenyl)-1,3-thiazol-2-yl]-1-(2,4-difluorophenyl)-1-(1H-1,2,4-triazol-1-ylmethyl)propyl}-oxy]methyl phosphate obtained in Production Example 1 was dissolved in 161 mL of methanol, and the mixture was cooled at a bath temperature of −20° C. 250 mL of concentrated hydrochloric acid was added dropwise over a period of 21 minutes, the reaction mixture was allowed to react for 4 hours at 0° C., and this product was added to a mixture of 700 mL of ethyl acetate and 1795 mL of an aqueous solution of 264 g of $K_2HPO_4$ and 542 g of $Na_2HPO_4$ dodecahydrate. The upper layer was decanted off and washed with 1 L of 5% saline, and then extracted two times with 1030 mL of 10% aqueous $K_3PO_4$. The $K_3PO_4$ extraction layer was transferred to a 3 L flask, 570 mL of butyl acetate was added thereto, and 210 mL of a 5N HCl aqueous solution was added dropwise while stirring. The pH of the aqueous layer here was 2.8. The organic layer was then washed with 570 mL of 5% saline. 89 mL of an aqueous solution in which 30.82 g of lysine had been dissolved was added, and the lower layer was separated off. 111 mL of ethanol was added to the aqueous lysine extraction layer, and 41 mL of acetic acid was added thereto. Then 337 mL of ethanol, 38 mL of water, and 14 mL of acetic acid were added thereto, and this product was transferred to a 3 L flask. 1345 mL of ethanol was added, then 400 mg of seed crystals were added thereto, and the system was stirred for 6 hours at 40° C., after which the mixture was stirred for 60 hours with the bath temperature set at 25° C., and the crystals thus produced were filtered off. The crystals were washed with 160 mL of ethanol and dried for 2 hours at a bath temperature of 50° C., which gave 64.5 g (58% yield) of the titled compound as an ethanol solvate as yellowish-white crystals.

$^1$H-NMR (D$_2$O, 400 MHz) δ: 1.21 (t, J=7 Hz, 3H), 1.26 (d, J=7 Hz, 3H), 1.51 (m, 2H), 1.75 (m, 2H), 1.93 (m, 2H), 3.05 (t, J=7 Hz, 2H), 3.68 (q, J=7 Hz, 2H), 3.78 (t, J=6 Hz, 1H), 3.85 (q, J=7 Hz, 1H), 5.10 (d, J=16 Hz, 1H), 5.17 (d, J=16 Hz, 1H), 5.25 (dd, J=8, 6 Hz, 1H), 5.41 (dd, J=8, 7 Hz, 1H), 6.80 (m, 1H), 6.83 (m, 1H), 7.15 (m, 1H), 7.57 (d, J=8 Hz, 2H), 7.66 (s, 1H), 7.71 (d, J=8 Hz, 2H), 7.89 (s, 1H), 8.70 (s, 1H)

Example 1

0.2 g of magnesium hydroxide carbonate was mixed with 1.0 g of the [2-[4-(4-cyanophenyl)-1,3-thiazol-2-yl]-1-(2,4-difluorophenyl)-1-(1H-1,2,4-triazol-1-ylmethyl)propyl}-oxy]methyl dihydrogenphosphate monolysine salt obtained in Production Example 2 (hereinafter referred to simply as "compound A") and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 2

0.2 g of magnesium hydroxide was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 3

0.2 g of magnesium oxide was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 4

0.2 g of sodium carbonate was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 5

0.2 g of sodium hydrogencarbonate was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 6

0.2 g of calcium silicate was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 7

0.2 g of calcium carbonate was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 8

0.2 g of arginine was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 9

0.2 g of calcium stearate was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 10

0.2 g of trisodium citrate was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Example 11

0.2 g of sodium benzoate was mixed with 1.0 g of compound A and 0.8 g of spray-dried mannitol (Parteck M200 from Merck). 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Comparative Example 1

1.0 g of compound A and 1.0 g of spray-dried mannitol (Parteck M200 from Merck) were mixed. 200 mg of this mixture was weighed out, tablets were produced using a compression moldability analyzer (Tabflex from Okada Seiko), which gave tablets with a weight of 200 mg and a diameter of 11.3 mm and containing 100 mg of compound A.

Test Example 1

The tablets produced in Examples 1 to 12 and Comparative Example 1 were stored for 1 week in an open container at a temperature of 60° C. and a relative humidity of 75%, and the amount of compound A remaining in the tablets was measured by high performance liquid chromatography (HPLC). These results are given in Table 1.

HPLC Conditions:
Detector: UV absorptiometer (measurement wavelength: 282 nm)
Column: a stainless steel tube with an inside diameter of 4.6 mm and a length of 5 cm, packed with octadecylsilylated silica gel for 3 μm liquid chromatography (L-Column ODS (Chemical Evaluation and Research Institute))
Column temperature: 40° C.
Mobile phase: A phase: 30 mM ammonium acetate
B phase: acetonitrile
Flux: 1.5 mL/minute
Gradient Conditions:

TABLE 1

| Time (minutes) | Proportion of mobile phase B liquid |
|---|---|
| 0 | 20 |
| 12 | 80 |
| 12.1 | 20 |
| 17 | stop |

Injected amount: 5 μL
Sample rack temperature: 20° C.
Analysis time: 17 minutes

TABLE 2

| Number | Basic substance | Percentage remaining | |
|---|---|---|---|
| | | Initial | After storage |
| Example 1 | magnesium hydroxide carbonate | 99.71 | 97.85 |
| Example 2 | magnesium hydroxide | 99.70 | 97.86 |
| Example 3 | magnesium oxide | 99.78 | 98.9 |
| Example 4 | sodium carbonate | 99.69 | 88.85 |
| Example 5 | sodium hydrogencarbonate | 99.73 | 95.11 |
| Example 6 | calcium silicate | 99.74 | 93.10 |
| Example 7 | calcium carbonate | 99.74 | 85.75 |
| Example 8 | Arginine | 99.71 | 96.62 |
| Example 9 | calcium stearate | 99.69 | 83.07 |
| Example 10 | trisodium citrate | 99.72 | 84.45 |
| Example 11 | sodium benzoate | 99.72 | 87.24 |
| Comp. Ex. 1 | — | 99.71 | 75.55 |

As shown in Table 1, adding the various basic substances clearly increased the percentage by which compound A remained. That is, when compound A was formulated, a pharmaceutical composition with improved storage stability could be produced.

Example 12

1275 g of compound A, 255.0 g of calcium silicate, 127.5 g of croscarmellose sodium, 255.0 g of magnesium oxide, and 331.5 g of mannitol were mixed in a high shear granulator (Super Mixer from Kawata). A 7:1 (w/w) mixture of ethanol and water was added to this mixed powder, and this mixture was granulated. The granules were dried in a tray dryer (made by Powrex), and was sized with a sieve attached mill (Power Mill from Showa Giken). 255.0 g of croscarmellose sodium and 51.0 g of magnesium stearate were added to the sized powder, and the components were mixed with a rotary mixer (tumbler mixer). The mixed powder was put in a tableting machine (HT-CVX-SS II from Hata Iron Works), and non-coated tablets were obtained. These non-coated tablets were given a film coating by the conventional method using a film coating machine (Hicoater Labo from Freund).

Example 13

5.0 g of compound A, 0.3 g of popidone, 1.5 g of croscarmellose sodium, 0.1 g of magnesium oxide, and 1.75 g of mannitol were mixed in a mortar. A 7:1 (w/w) mixture of ethanol and water was added to this mixed powder, and this mixture was granulated. The granules were dried in a constant-temperature forced-air dryer (from Eyela) and passed through a 1 mm-mesh sieve to size the particles. 1.2 g of carmellose, 0.05 g of calcium silicate, and 0.1 g of magnesium stearate were added to the sized powder and mixed. 170 mg of this mixture was collected and put in a compression moldability analyzer (Tabflex from Okada Seiko), which gave tablets with a weight of 170 mg and a diameter of 7.5 mm and containing 85 mg of compound A.

Example 14

5.0 g of compound A, 0.3 g of popidone, 1.5 g of croscarmellose sodium, 0.3 g of magnesium oxide, and 1.55 g of mannitol were mixed in a mortar. A 7:1 (w w) mixture of ethanol and water was added to this mixed powder, and this mixture was granulated. The granules were dried in a constant-temperature forced-air dryer (from Eyela) and passed through a 1 mm-mesh sieve to size the particles. 1.2 g of carmellose, 0.05 g of calcium silicate, and 0.1 g of magnesium stearate were added to the sized powder and mixed. 170 mg of this mixture was collected and put in a compression moldability analyzer (Tabflex from Okada Seiko), which gave tablets with a weight of 170 mg and a diameter of 7.5 mm and containing 85 mg of compound A.

Example 15

5.0 g of compound A, 0.3 g of popidone, 1.5 g of croscarmellose sodium, 0.5 g of magnesium oxide, and 1.35 g of mannitol were mixed in a mortar. A 7:1 (w/w) mixture of ethanol and water was added to this mixed powder, and this mixture was granulated. The granules were dried in a constant-temperature forced-air dryer (from Eyela) and passed through a 1 mm-mesh sieve to size the particles. 1.2 g of carmellose, 0.05 g of calcium silicate, and 0.1 g of magnesium stearate were added to the sized powder and mixed. 170 mg of this mixture was collected and put in a compression moldability analyzer (Tabflex from Okada Seiko), which gave tablets with a weight of 170 mg and a diameter of 7.5 mm and containing 85 mg of compound A.

Example 16

5.0 g of compound A, 0.3 g of popidone, 1.5 g of croscarmellose sodium, 0.05 g of sodium hydroxide, and 1.8 g of mannitol were mixed in a mortar. A 7:1 (w/w) mixture of ethanol and water was added to this mixed powder, and this mixture was granulated. The granules were dried in a constant-temperature forced-air dryer (from Eyela) and passed through a 1 mm-mesh sieve to size the particles. 1.2 g of carmellose, 0.05 g of calcium silicate, and 0.1 g of magnesium stearate were added to the sized powder and mixed. 170 mg of this mixture was collected and put in a compression moldability analyzer (Tabflex from Okada Seiko), which gave tablets with a weight of 170 mg and a diameter of 7.5 mm and containing 85 mg of compound A.

Example 17

5.0 g of compound A, 0.3 g of popidone, 1.5 g of croscarmellose sodium, 0.1 g of sodium hydroxide, and 1.75 g of mannitol were mixed in a mortar. A 7:1 (w/w) mixture of ethanol and water was added to this mixed powder, and this mixture was granulated. The granules were dried in a constant-temperature forced-air dryer (from Eyela) and passed through a 1 mm-mesh sieve to size the particles. 1.2 g of carmellose, 0.05 g of calcium silicate, and 0.1 g of magnesium stearate were added to the sized powder and mixed. 170 mg of this mixture was collected and put in a compression moldability analyzer (Tabflex from Okada Seiko), which gave tablets with a weight of 170 mg and a diameter of 7.5 mm and containing 85 mg of compound A.

Comparative Example 2

5.0 g of compound A, 0.3 g of popidone, 1.5 g of croscarmellose sodium, and 1.85 g of mannitol were mixed in a mortar. A 7:1 (w/w) mixture of ethanol and water was added to this mixed powder, and this mixture was granulated. The granules were dried in a constant-temperature forced-air dryer (from Eyela) and passed through a 1 mm-mesh sieve to size the particles. 1.2 g of carmellose, 0.05 g of calcium silicate, and 0.1 g of magnesium stearate were added to the sized powder and mixed. 170 mg of this mixture was collected and put in a compression moldability analyzer (Tabflex from Okada Seiko), which gave tablets with a weight of 170 mg and a diameter of 7.5 mm and containing 85 mg of compound A.

Test Example 2

The tablets produced in the above examples and comparative examples were stored for 6 days in an open container at a temperature of 60° C. and a relative humidity of 75%, and the amount of compound A remaining in the tablets was measured by high performance liquid chromatography (HPLC). These results are given in Table 4.

HPLC Conditions:
Detector: UV absorptiometer (measurement wavelength: 287 nm)
Column: a stainless steel tube with an inside diameter of 4.6 mm and a length of 15 cm, packed with octylated silica gel for 3 μm liquid chromatography (Capcell Pak C8 DD from Shiseido)
Column temperature: 45° C.
Mobile phase: A phase: 30 mM ammonium acetate solution/acetonitrile (900:100 v/v)
B phase: 30 mM ammonium acetate solution/acetonitrile (100:900 v/v)
Flux: 1.0 mL 1 minute
Gradient Conditions:

TABLE 3

| Time (minutes) | Proportion of mobile phase B liquid |
| --- | --- |
| 0 | 20 |
| 25 | 20 |
| 45 | 65 |
| 50 | 65 |
| 52.5 | 20 |
| 60 | 20 |

Injected amount: 10 μL
Sample rack temperature: 15° C.
Analysis time: 60 minutes

TABLE 4

| Number | Basic substance | Percentage remaining after storage |
| --- | --- | --- |
| Example 13 | magnesium oxide, 2.0% (w/w) vs. compound A | 87.47 |
| Example 14 | magnesium oxide, 6.0% (w/w) vs. compound A | 94.84 |
| Example 15 | magnesium oxide, 10.0% (w/w) vs. compound A | 96.10 |
| Example 16 | sodium hydroxide, 1.0% (w/w) vs. compound A | 69.78 |
| Example 17 | sodium hydroxide, 2.0% (w/w) vs. compound A | 83.65 |
| Comp. Ex. 2 | — | 67.13 |

As shown in the table 4, adding magnesium oxide or sodium hydroxide in an amount of at least 2.0% based on compound A increased the percentage by which compound A remained.

INDUSTRIAL APPLICABILITY

According to the present invention, a stable pharmaceutical composition containing the azole-based compound that has antifungal activity can be obtained. The pharmaceutical composition according to the present invention is absorbed well into the body, and exhibits an excellent antifungal action. In addition, according to the present invention, stable tablets, granules, capsules, and the like can be produced, so an antifungal agent can be given by systemic administration by an easy method, and is useful as a therapeutic agent for various mycoses such as deep mycoses.

We claim:

1. A solid pharmaceutical composition, comprising:
an azole-based compound; and
a basic substance;
wherein the azole-based compound is [[2-[4-(4-cyanophenyl)-1,3-thiazol-2-yl]-1-(2,4-difluorophenyl)-1-(1H-1,2,4-triazol-1-ylmethyl)propyl]oxy]methyl dihydrogenphosphate monolysine salt,
wherein the basic substance is an inorganic base or a basic amino acid,
wherein the inorganic base is at least one selected from the group consisting of magnesium hydroxide carbonate, sodium hydrogencarbonate, magnesium hydroxide, magnesium oxide, and calcium silicate;
wherein the basic amino acid is arginine, and
wherein the basic substance is present in the composition in an amount of 2 to 25% (w/w) with respect to the azole-based compound.

2. The solid pharmaceutical composition according to claim 1, wherein the basic substance exhibits a pH of at least 8.0 when made into a 1% aqueous solution or a 1% aqueous suspension.

3. The solid pharmaceutical composition according to claim 1, wherein the basic substance exhibits a pH of at least 10.0 when made into a 1% aqueous solution or a 1% aqueous suspension.

4. The solid pharmaceutical composition according to claim 1, wherein the pharmaceutical composition is an antifungal agent.

5. The solid pharmaceutical composition according to claim 1, wherein the basic substance exhibits a pH of at least 8.0 when made into a 1% aqueous solution or a 1% aqueous suspension; and
wherein the pharmaceutical composition is an antifungal agent.

6. The solid pharmaceutical composition according to claim 1, wherein the solid pharmaceutical composition is in the form of a tablet, granule, or capsule.

7. The solid pharmaceutical composition according to claim 1, wherein the basic substance is present in the composition in an amount of 2 to 20% (w/w) with respect to the azole-based compound.

8. A method for stabilizing a solid pharmaceutical composition, the method comprising the step of:
mixing a basic substance with an azole-based compound;
wherein the azole-based compound is [[2-[4-(4-cyanophenyl)-1,3-thiazol-2-yl]-1-(2,4-difluorophenyl)-1-(1H-1,2,4-triazol-1-ylmethyl)propyl]oxy]methyl dihydrogenphosphate monolysine salt,
wherein the basic substance is an inorganic base or a basic amino acid,
wherein the inorganic base is at least one selected from the group consisting of magnesium hydroxide carbonate, sodium hydrogencarbonate, magnesium hydroxide, magnesium oxide, and calcium silicate;
wherein the basic amino acid is arginine, and
wherein the basic substance is present in the composition in an amount of 2 to 25% (w/w) with respect to the azole-based compound.

9. A process for producing the solid pharmaceutical composition according to claim 1, the process comprising the step of:

mixing the basic substance with the azole-based compound.

10. The method of claim 8, wherein the solid pharmaceutical composition is in the form of a tablet, granule, or capsule.

11. The method according to claim 8, wherein the basic substance is present in the solid pharmaceutical composition in an amount of 2 to 20% (w/w) with respect to the azole-based compound.

* * * * *